United States Patent [19]

Thiele et al.

[11] Patent Number: 4,668,786

[45] Date of Patent: * May 26, 1987

[54] P-FLUOROBENZOYL-PIPERIDINO ALKYL THEOPHYLLINE DERIVATIVES

[75] Inventors: Kurt Thiele; Felix Geissmann; Ludwig Zirngibl; Ulrich Jahn, all of Zofingen, Switzerland

[73] Assignee: Siegfried Aktiengesellschaft, Zofingen, Switzerland

[ * ] Notice: The portion of the term of this patent subsequent to Jul. 29, 2003 has been disclaimed.

[21] Appl. No.: 813,439

[22] Filed: Dec. 26, 1985

Related U.S. Application Data

[63] Continuation-in-part of Ser. No. 474,230, Mar. 11, 1983, Pat. No. 4,603,204.

[30] Foreign Application Priority Data

Jul. 20, 1981 [CH] Switzerland .......................... 4739/81

[51] Int. Cl.$^4$ .................... C07D 473/08; A61K 31/52
[52] U.S. Cl. .................................... 544/267; 544/268; 544/269
[58] Field of Search ................ 544/267, 268, 269, 263

[56] References Cited

U.S. PATENT DOCUMENTS 4,284,633  8/1981  Friebe et al. .......................... 544/267
4,603,204  7/1986  Thiele et al. .......................... 544/267

Primary Examiner—Nicholas S. Rizzo
Attorney, Agent, or Firm—Jordan and Hamburg

[57] ABSTRACT

New derivatives of theophylline having the formula

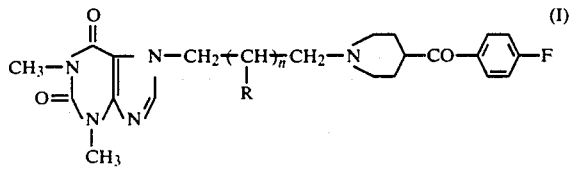

wherein R is hydrogen or a hydroxy group, and n is an integer of $0 \leq n \leq 3$ and/or the pharmaceutically acceptable, acid addition salts thereof, exhibit in addition to other properties, histamine-serotinine- bradykynine-antagonistic, anti-anaphylactic and β-adrenergic stimulating effects.

6 Claims, No Drawings

P-FLUOROBENZOYL-PIPERIDINO ALKYL THEOPHYLLINE DERIVATIVES

This is a continuation-in-part application of Ser. No. 474,230 filed Mar. 11, 1983 now U.S. Pat. No. 4,603,204.

BACKGROUND OF THE INVENTION

The invention relates to new derivatives of theophylline.

The pharmacodynamical properties of the derivatives of xanthine have caused the pharmaceutical industry to also study intensively theophylline and its derivatives because of their influence upon the heart and the circulation. At the turn of the century, one already began to substitute the theophylline-molecule with basic groups in order to counteract its low solubility in water, and as a consequence, a large number of theophylline derivatives have been synthesized, some with hydrophylic substituents in the 7-position, or some in the form of addition- or double salts. Many of these have found their place as medical substances in therapy, where direct or indirect use was made of their advantageous influence upon circulation, in order to use them as vasocoronary, bronchio-dilators or antiasthmatics, as long as they are not salts or double-salts or similar substances, whose additive ions or molecular components (as, for instance in the case of ephedrine) exhibit specific individual components of effect and in that sense include additive components of effect or may even overshadow and dominate the effect of theophylline. Recently 7-(4-aminopiperidino-propyl)-theophyllines with antiallergic and antihistamic effects have been described in DE-OS 29 22 159.

SUMMARY OF THE INVENTION

The invention relates to new p-fluorobenzoyl-piperidino alkyl derivatives of theophylline, having the formula

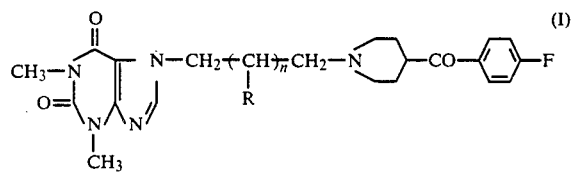

wherein R is hydrogen or a hydroxy group, and n is an integer of $0 \leq n \leq 3$ and/or the pharmaceutically acceptable, acid addition salts thereof.

These compounds may be prepared according to a process being characterized by reacting a theophylline which is substituted in the 7-position with a group of the formula:

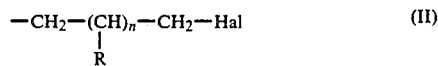

(where R and n denote the same as in the aforenamed formula (I)) and where "Hal" denotes a halogen, preferably chlorine or bromine) with a base of formula

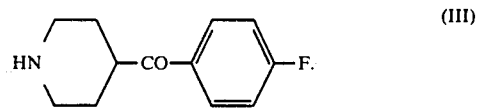

The reaction may be initiated at elevated temperature with or without the use of a solvent (isopropanol, for instance). When operating without a solvent, the base materials are held at the temperature of a molten mixture, until periodically taken samples of the reaction mixture show by thin layer chromatography that the reaction is substantially finished. In that case, one advantageously uses the base as an initial material of formula (III) in double or triple excess for binding the split-off hydrogen halide.

The starting materials of formula (II) are known and may be easily obtained; when so desired, they may be synthesized in a known manner (see Arzneim.-Forsch. 27,5 ff. (1977)) by condensation of theophylline with the respective alkylene dihalides or epichlorhydrin, respectively. The bases of the formula (III) may also be obtained as commercial products in the form of their hydrochloride salts, from which they may be liberated by treatment with alkali metal hydroxides in a manner known to the expert prior to their use for the reaction according to the invention.

It has been shown that the derivatives of theophylline according to the invention surprisingly exhibit versatile pharmacological effects.

The substances according to the invention were shown to have outstanding histamine-, serotonine- and bradykinine-, antagonistical, blood pressure lowering, antianaphylactical and β-adrenergic stimulating properties and which distinctly differ by this broad spectrum of activity from the conventional derivatives of theophylline. Based upon the aforementioned pharmacodynamical properties, therapeutical use can be found as migraine remedies, broncholytics, antiallergenics, antiphylogistics, analgesics and antihypertonics. The substances having the codes Sgd 195-78 (see the following example 1) and Sgd 144-80 (see example 2) were especially promising. Thus, according to current knowledge, those compounds of formula (I) may be favored, where R denotes a hydrogen atom and n the number 0 or 1 (preferably 0), while, however, also the compounds of formula (I) having n=2 and n=3 still are of significant activity.

DETAILED DESCRIPTION OF THE INVENTION

In the structural formulae of the following examples, "Th" denotes the theophylline group, which is bound in the 7-position to the partial structure mentioned in the individual example.

EXAMPLE 1

7-[2-[4-(p-fluorobenzoyl)-piperidino]-ethyl]-theophylline (Sgd 195-78)

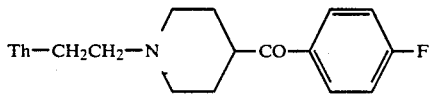

25.6 g (0.124M) 4-(p-fluorobenzoyl)-piperidine is heated together with 15.0 g (0.062M) 7-(2-chloroethyl)-theophylline in the solid state in a round flask to 100° C. during one hour. It is cooled down to 60° C. and ethyl acetate is added while stirring until a homogeneous suspension is present. After cooling and filtering off of the separated fluorobenzoylpiperidine hydrochloride, 2n hydrochloric acid is added to the filtrate for the precipitation of the raw product. The residue, separated by filtration, is washed twice, each time with water and ethyl acetate, and subsequently a layer of ethyl acetate is added and 100 ml sodium hydroxide solution is added. After agitation and separation of the phases, the principal amount of the product resides in the organic phase; in order to obtain additional amounts of product, the aqueous phase is shaken twice, each with 100 ml ethyl acetate. The combined organic phases are washed with saturated NaCl solution, treated with activated carbon, dried over $MgSO_4$ and filtered. After distilling off of the solvent, the filtrate yields 20.4 g (80%) raw crystalline product. For additional purification, the residue is suspended in 250 ml carbon tetrachloride and heated at reflux temperature. The dark brown solution obtained thereby, becomes light orange after treatment with activated carbon and on cooling yields 14.5 g white product with an mp of 143°–145° C., which is shown to be pure by thin layer chromatography.

| | $C_{21}H_{24}FN_5O_3$ | | 413.46 | |
|---|---|---|---|---|
| calc. | C 61.00 | H 5.85 | N 16.94 | F 4.60 |
| fd. | C 60.80 | H 5.66 | N 17.11 | F 4.46 |

A pure product of identical composition according to thin layer chromatography which melts under decomposition at 248° C. was obtained by heating the starting materials mixed at the same ratio to 120° C. for five hours, subsequently boiling 7 hours in n-propanol, corresponding working-up and crystallizing from carbon tetrachloride.

| | $C_{21}H_{24}FN_5O_3$ | | | |
|---|---|---|---|---|
| calc. | C 61.00 | H 5.85 | N 16.94 | F 4.60 |
| fd. | C 60.53 | H 5.63 | N 16.49 | F 4.06 |

EXAMPLE 2

7-[3-[4-(p-fluorobenzoyl)-piperidino]-propyl]-theophylline (Sgd 144-80)

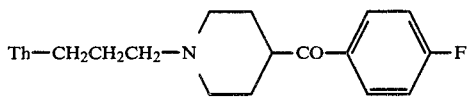

10.2 g 4-(p-fluorobenzoyl)-piperidine and 16.5 g 7-(chloropropyl)-theophylline are carefully mixed in the solid state and heated to 100° C. in a round flask in an oil bath. The mixture at first results in a clear melt, subsequently begins to crystallize and then changes into a solid mass. It is allowed to cool after 10 minutes, dissolved in ethyl acetate and 2n hydrochloric acid is added, whereby a dark oil separates in the organic phase, crystallizing on standing overnight. By recrystallizing with 100 ml carbon tetrachloride, an initially oily then crystallizing substance is obtained, 7.4 g of the product with an mp of 114° to 119° C. (yield: 43.5%)

| | $C_{22}H_{26}FN_5O_3$ | | 427.5 | |
|---|---|---|---|---|
| calc. | C 61.81 | H 6.13 | N 16.38 | F 4.45 |
| fd. | C 61.90 | H 6.01 | N 16.40 | F 4.29 |

The 7-(3-chloropropyl)-theophylline, used as a starting material, may be obtained in a known manner, for instance by the reaction of theophylline with 1,3-bromo-chloropropane.

EXAMPLE 3

7-[3-[4-(p-fluorobenzoyl)-piperidino]-2-hydroxypropyl]theophylline hydrate (Sgd 145-80)

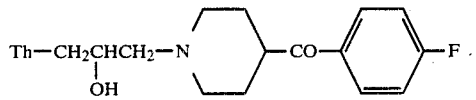

8 g 7-(3-chloro-2-hydroxpropyl)-theophylline, mixed with 12.16 g 4-(fluorobenzoyl)-piperidine are maintained for 1 hour in an oil bath at a temperature of 100° C., whereby the viscosity of the melt, which is initially highly fluid and clear, rises after 30 minutes. After cooling, the mixture is treated for 30 minutes with ethyl acetate while being vigorously stirred. The solution, thereby produced, is separated by filtering, from the separated 4-(p-fluorobenzoyl)-piperidine hydrochloride, and 2n hydrochloric acid is added. After phase separation, the aqueous phase is shaken with ethyl acetate, made alkaline by the addition of concentrated sodium hydroxide solution and extracted twice with ethyl acetate. The substance crystallizing from the extract exhibits a melting point of 132°–138° C. after recrystallization from chloroform-ethanol (9:1) and drying in a high vacuum.

| | $C_{22}H_{26}FN_5O_4.H_2O$ | | 461.5 | |
|---|---|---|---|---|
| calc. | C 57.26 | H 6.12 | N 15.18 | F 4.12 |
| fd. | C 57.54 | H 6.15 | N 15.52 | F 4.10 |

The 7-(3-chloro-2-hydroxypropyl)-theophylline may be prepared in a known manner by the reaction of theophylline and epichlorohydrin.

EXAMPLE 4

7-(4-(4-(p-fluorobenzoyl)-piperidino)-butyl-theophylline (Sgd 1-85)

45 g theophylline, 145 ml N,N-dimethylformamide, 34.6 g potassium carbonate and 59.4 g dibromobutane are charged into a glass flask having a capacity of 1 l and heated to a temperature of 35° C. The suspension thus obtained is stirred for 6 h at 35° C. The reaction mixture then is added with 270 ml water, and is allowed to stay overnight in a refrigerator at about 4° C. The crystalline product thus obtained is separated from the liquid phase by vacuum filtration with 60 ml water and well dried by maintaining the vacuum on the filtrate side of the filter.

Since in the present example instead of the more effective but also more expensive 1-bromo-4-chlorobutane the dibromobutane was used in addition to the 7-(4-bromobutyl)-theophylline also some di-theophylline-butane was formed. For the purification of the crude 7-(4-bromobutyl)-theophylline the crude crystals were taken up in 400 ml ethanol and heated to 50° C. while stirring. Stirring is continued for 20 min at 50° C. The suspension is filtered still warm and washed with 50 ml ethanol. The ethanolic solution obtained as a filtrate in this operation is then evaporated to dryness, and the solid residue is admixed with 150 ml n-hexane. After washing the suspension thus obtained, the liquid phase once again is filtered off, while washing the remaining crystals with 50 ml n-hexane.

The purified product thus obtained has a melting point of 96° C. The purified product finally is obtained in form of a white powdery material in an amount of 27.4 g. The 7-(4-bromobutyl)-theophylline then is reacted with 4-(fluorobenzoyl)-piperidine. For this purpose 28.5 g 4-(fluorobenzoyl)-piperidine is dissolved in 900 ml hot water at about 55° C. in a glass flask having a capacity of 1 l. While stirring, 0.7 g activated charcoal are added. Having then filtered off the charcoal, a light yellow solution is obtained which is transferred into a glass flask having a capacity of 2 l. While stirring, 20.1 g potassium carbonate followed by 30 g 7-(4-bromobutyl)-theophylline are added thereto. The reaction mixture is heated to 100° C. and kept at this temperature for 3 h. After then cooling down to about 50° C. 250 ml iso-butylmethyl ketone are given into the reaction mixture. after the separation of the phases the lower aqueous phase is separated in a separatory funnel from the upper organic phase, which latter then is evaporated to dryness under reduced pressure. The solid residue is taken up with petroleum ether, from which suspension the solid material is separated by vacuum filtration. The yield is 21 g of crude product.

The crude product thus obtained is purified in a chromatographic column on silica using a chloroform methanol (9:1) solvent system, and finally twice is recrystallized from methanol. The product thus obtained in a yield of 13 g is a highly pure 7-(4-(4-(p-fluorobenzoyl)-piperidino)-butyl)-theophylline having a melting point of 137° C.

EXAMPLE 5

7-(5-(4-(p-fluorobenzoyl)-piperidino)-pentyl)-theophylline (Sgd 2-85)

The method of example 4 is repeated with the exception that 63.3 g 1.5-dibromopentane rather than 59.4 g 1.4-dibromobutane are reacted with the theophylline.

After chromatographic purification and crystallizing the crude product twice from methanol 15.8 g of 99% pure 7-(5-(4-(p-fluorobenzoyl)-piperidino)-pentyl-theophylline are obtained having a melting point of 125° C.

We claim:
1. A theophylline derivative of the formula

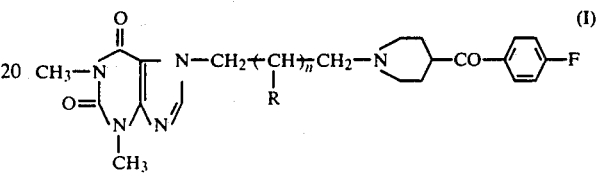

wherein
R is hydrogen or a hydroxy group, and
n is an integer of $0 \leq n \leq 3$
and/or the pharmaceutically acceptable, acid addition salts thereof.
2. The compound of claim 1 which is 7-(2-(4-(p-fluorobenzoyl)-piperidino)ethyl)theophylline.
3. The compound of claim 1 which is 7-(3-(4-(p-fluorobenzoyl)-piperidino)propyl)theophylline.
4. The compound of claim 1 which is 7-(3-(4-(p-fluorobenzoyl)-piperidino)-2-hydroxypropyl)-theophylline hydrate.
5. The compound of claim 1 which is 7-(4-(4-(p-fluorobenzoyl)-piperidino)butyl)theophylline.
6. The compound of claim 1 which is 7-(5-(4-(p-fluorobenzoyl)-piperidino)pentyl)theophylline.

* * * * *